US008779182B2

(12) United States Patent
Koole et al.

(10) Patent No.: US 8,779,182 B2
(45) Date of Patent: Jul. 15, 2014

(54) PROCESS FOR THE SIMULTANEOUS PRODUCTION OF DIFFERENT MIXTURES OF DIISOCYANATE ISOMERS OF THE DIPHENYLMETHANE SERIES

(75) Inventors: Johannes Lodewijk Koole, Kessel-Lo (BE); Adolf Daan Zijl, Tervuren (BE); Robert Henry Carr, Bertem (BE)

(73) Assignee: Huntsman International LLC, The Woodlands, TX (US)

( * ) Notice: Subject to any disclaimer, the term of this patent is extended or adjusted under 35 U.S.C. 154(b) by 410 days.

(21) Appl. No.: 13/122,162

(22) PCT Filed: Oct. 1, 2009

(86) PCT No.: PCT/EP2009/062724
§ 371 (c)(1),
(2), (4) Date: Apr. 1, 2011

(87) PCT Pub. No.: WO2010/040675
PCT Pub. Date: Apr. 15, 2010

(65) Prior Publication Data
US 2011/0224456 A1    Sep. 15, 2011

(30) Foreign Application Priority Data
Oct. 6, 2008   (EP) .................................... 08165930

(51) Int. Cl.
*C07C 263/00* (2006.01)
*C07C 263/20* (2006.01)

(52) U.S. Cl.
CPC .................................... *C07C 263/20* (2013.01)
USPC ........................................................ 560/352

(58) Field of Classification Search
CPC combination set(s) only.
See application file for complete search history.

(56) References Cited

U.S. PATENT DOCUMENTS 4,118,410 A * 10/1978 Friedel et al. ................. 560/352

FOREIGN PATENT DOCUMENTS

| DE | 196 51 215 C1 | 7/1978 |
| GB | 1 417 087 A | 12/1975 |
| GB | 1 423 993 A | 2/1976 |

* cited by examiner

*Primary Examiner* — Karl J Puttlitz
(74) *Attorney, Agent, or Firm* — Robert A. Diaz

(57) ABSTRACT

Process for the simultaneous and continuous production of two different mixtures of predominantly 4,4'-MDI and 2,4'-MDI in a single-step suspension melt crystallisation process whereby a mixed diisocyanate feed stream [MIx] is used to produce simultaneously two mixed diisocyanate streams [MIy] and [MIz] wherein x=80 to 92, y=97 to 99 and z=60 to 80 preferably x=82 to 88, y=97.2 to 98.5 and z=63 to 70 where x, y and z are percentages by weight of the 4,4'-MDI isomer contained in the diisocyanate isomer mixture.

6 Claims, 11 Drawing Sheets

PROCESS FOR THE SIMULTANEOUS PRODUCTION OF DIFFERENT MIXTURES OF DIISOCYANATE ISOMERS OF THE DIPHENYLMETHANE SERIES

CROSS-REFERENCE TO RELATED APPLICATIONS

This application is the National Phase of International Application PCT/EP2009/062724 filed Oct. 1, 2009 which designated the U.S. and which claims priority to EP App. Ser. No. 08165930.2 filed Oct. 6, 2008. The noted applications are incorporated herein by reference.

The present invention relates to a process for the simultaneous production of different mixtures of diisocyanate isomers of the diphenylmethane series.

Aromatic isocyanates are important raw materials for the production of polyurethane materials. In this connection the diisocyanates and polyisocyanates of the diphenylmethane series (MDI) play the greatest role, quantitatively. Polyisocyanates of the diphenylmethane series are understood to denote isocyanates and isocyanate mixtures of the following type:

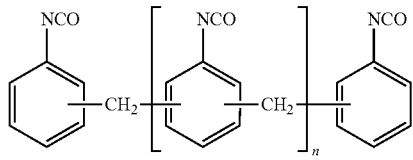

where n denotes a natural number greater than or equal to zero.

Similarly, polyamines of the diphenylmethane series are understood to denote compounds and compound mixtures of the following type:

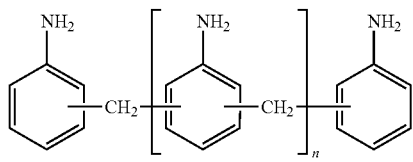

where n denotes a natural number greater than or equal to zero.

It is known that diisocyanates and polyisocyanates of the diphenylmethane series (MDI) are produced by phosgenation of the corresponding diamines and polyamines of the diphenylmethane series (MDA). The diamines and polyamines of the diphenylmethane series (MDA) are themselves produced by condensation of aniline and formaldehyde. The corresponding diisocyanates, 2,2'-MDI, 2,4'-MDI and 4,4'-MDI, which are described in the specialist circles as 2-ring (i.e. bi-nuclear) compounds of MDI (i.e. diisocyanates of the diphenylmethane series), are obtained by phosgenation of diamines of the diphenylmethane series. During the condensation of aniline and formaldehyde, the 2-ring i.e. (bi-nuclear) MDA (methylenediphenyldiamine), however, also continues to react further with formaldehyde and aniline to form higher-nuclear (i.e. poly-nuclear or poly-ring) MDA types, which after the phosgenation constitute the polynuclear content in the polymeric MDI (i.e. polyisocyanates of the diphenylmethane series).

The crude MDI mixture produced in the phosgenation can be separated in the polymer/monomer separation by means of simple evaporation or distillation into 2-nuclear-MDI (i.e. monomeric MDI) and a polymer-MDI fraction (i.e. polymeric MDI or PMDI). The isomer mixture of the 2-nuclear-MDI fraction contains, in addition to the diisocyanates 2,2'-MDI, 2,4'-MDI and 4,4'-MDI, some secondary components such as solvent residues or phenyl isocyanate derivatives.

Many different process variations are known for the production and work-up of the polyamine mixture, the production and work-up of the polyisocyanate mixture and the production of a diisocyanate or predominantly diisocyanate stream. All these preceding methods are suitable for the subsequent application of the present invention.

The monomeric 2-nuclear-MDI fraction is separated, according to the prior art, by distillation or by crystallisation into a stream which is essentially the pure or substantially pure 4,4'-MDI isomer and into a Mixed Isomer (MI) stream which is a mixture comprising 2,4'-MDI and 4,4'-MDI. The pure or substantially pure 4,4'-MDI isomer is available commercially typically with an isomer purity of 98-99% 4,4'-MDI and is known as Pure MDI.

Various Mixed Isomer streams can be produced with varying amounts of the two MDI isomers and which are available commercially.

The Pure MDI and Mixed Isomer monomeric products are supplied as polyurethane raw materials to the world market, or they are processed further with polymeric MDI into mixed products and/or with polyethers or polyesters or the like into prepolymers or by further reaction to form variants, etc. as is well known in the art. Many different Mixed Isomer products are useful both in their own right, for the production of variants and prepolymers and as components of various isocyanate product blends. It is possible to make very high purity ["Super Pure MDI"] 4,4'-MDI: even 99.99% 4,4'-MDI is known [Mostecky, Jiri; Pecka, Karel: Czech. Cz144738 15 Feb. 1972] but the multiple purification steps generally required, either as distinct and separate steps or as "integral parts" of, for example, a sophisticated fractional distillation process makes this economically unattractive.

Due to the low volatility and high boiling points of the MDI isomers, distillation requires very low pressures and high temperatures. In addition, the relatively small differences between the volatilities of the individual MDI isomers requires the process to be operated with a high reflux. Distillation is therefore a complex and energy intensive process. Thus, a major advantage of crystallization over distillation generally is the significantly lower energy consumption. In the case of MDI the latent heat of fusion is less than a third of the latent heat of vaporization.

It is known in the art to purify certain chemicals, especially certain organic chemicals, by solidification, fractional solidification, and/or crystallization, to remove impurities from the chemicals. In solidification, fractional solidification and/or crystallization processes, the compound to be purified and the impurities are a component of a liquid medium. A change of conditions (such as removal of a solvent, or a change in temperature) is used to induce the compound to be purified to exceed its solubility in the medium, so as to induce solidification or crystallization. Preferably, the impurities remain substantially in the medium, and the solidified or crystallized compound is therefore purified. Solidification processes may be subdivided into layer processes, wherein solidification occurs on a solid surface, or suspension processes wherein the solid and/or crystals form as a suspension in the liquid medium. The general principals of solidification and/or crystallization are taught in treatises such as: Principles of Solidification by Bruce Chalmers (John Wiley & Sons 1964); "Fractional Crystallization", Process Technology Proceedings, 6, Industrial Crystallization 87, by S. J. Jancic (Proceedings of the 10th Symposium on Industrial Crystallization, Bechyne, Czechoslovakia, Sep. 21-25, 1987); and Fractional Solidification, by Zief et. al. (Marcel Dekker, Inc. 1967); which are hereby incorporated by reference.

Crystallization processes based on layer growth technologies, where crystals are grown on the wall of a heat exchanger, are well known and have been employed at a commercial scale for the production of MDI diisocyanate products. Static as well as dynamic crystallization processes can be used. Both technologies operate as batch processes. However, the selectivity of layer crystallization is limited, particularly when operating at economically beneficial rates whilst, in comparison, fractional distillation is capable of achieving high selectivity, leading to high product purity. However, operating fractional distillation processes for the purification of MDI isomers whether in single or multiple distillation columns and with or without divided columns is expensive in terms of the required process equipment.

It is also known in the art to purify certain chemicals by the technique of "melt crystallization." In melt crystallization, the compound to be purified typically comprises a major fraction, or preferably a high fraction of the mixture to be purified, but nevertheless contains (preferably minor) impurities. Solvents are not typically added to melt crystallization processes. The mixture (which may be a solid at ambient temperature) is maintained at a temperature above its melting point to form a liquid medium, then cooled below the melting point of the compound to be purified, to induce solidification or crystallization out of the "melt". If the solid and/or crystals are removed from the melt before all of the desired compound has crystallized (i.e. the liquid phase is fractionally solidified and/or crystallized), the impurities will concentrate in a liquid melt residue, that can be readily separated from the solid or crystals. The purity of crystals formed by melt crystallization processes can be very good. The general techniques and methods employed in melt crystallization have been discussed in treatises by Sloan et al., in "Techniques of Melt Crystallization", Techniques of Chemistry, vol. XIX (John Wiley & Sons, 1988); by Wynn in "Melt Crystallization" in Section 5.3 of Handbook of Separation Techniques for Chemical Engineers, 3d ed., (P. A. Scheitzer Ed., McGraw-Hill 1997), and by Toyokura et al., in "Crystallization from the Melt", Crystallization Technology Handbook, (Marcel Dekker, Inc. 1995), which are hereby incorporated by reference in their entireties.

A suspension/melt growth crystallization process consists of two units that are run continuously,
a) the crystallizer with a growth vessel where crystals are grown in suspension
b) the solid-liquid separator where crystals are separated from the melt.

In the crystalliser, crystal growth takes place in a growth vessel and heat is removed externally in a special heat exchanger that acts as a crystallizer. Super-saturation is created in the crystallizer by sub-cooling the mother liquor resulting in the formation of small crystals which are freely suspended in the mother liquor. Drum crystallizers and Scraped Surface Heat Exchangers are known to be used. Conventionally due to a large crystal surface area per unit volume, low growth rates can be applied which results in superior selectivity and thus very high crystal purity. The slurry of pure crystals in the mother liquor then passes to a solid-liquid separator.

It is generally known that, in the case of a slurry of suspension crystals, separation of suspension crystals and residual melt may also be carried out either exclusively, or after partial mechanical separation (in particular before use of a mechanical wash column) of residual melt, by means of a suitable washing liquid in a wash column in which the wash liquid is passed counter currently, to the suspension crystals. The washing liquid is optionally the Mother Liquor from which the pure crystals were originally formed.

In principle, the wash column types are divided into those with forced transport of the suspension crystal bed and those with gravity transport of the suspension crystals (a detailed description of the different wash column types is to be found, inter alia, in Chem.-Ing.-Techn. 57 (1985) No. 2, 91-102, in Chemical Engineering Science 50, 1995, No. 17, 2712 to 2729, Elsevier Science Ltd., in Applied Thermal Engineering 17, (1997) No. 8-10, 879-888, Published by Elsevier Science Ltd., and the citations stated in the abovementioned references). In wash columns with forced transport of the suspension crystal bed, at least one force other than gravitation in the transport direction is used for transporting the suspension crystal bed.

Inside the wash column, the suspension crystals are transported either from top to bottom or from bottom to top. The wash liquid is passed counter currently to the suspension crystals in the wash column. In the prior publications DE-A 19626839, DE-A 19740252, DE-A 19829477, DE-A 19832962, DE-A 19833049 and DE-A 19838845 inter alia water or aqueous acrylic acid is recommended as wash liquid to be used for crude acrylic acid suspensions. However, the disadvantage of these wash liquids is that, on the one hand, the purification effect is not completed satisfactorily and, on the other hand, they result in considerable loss of the desired pure product—such as acrylic acid.

As an alternative to the above mentioned procedure, it is also possible to melt the suspension crystals reaching the wash column in purified form at the end of their transport distance (the mother liquor is removed as a rule in the opposite part of the wash column), to remove only a portion of the resulting purified melt and to recycle the remaining amount of the purified melt as wash melt to the wash column and to do so counter currently to the suspension crystals fed to the wash column. Depending on the physical characteristics of the crystal suspension to be treated in the wash column, a purification effect may be achieved either on the basis of one or more mechanisms.

It may be argued that each cycle of the wash column is, in a sense, a small batch but the timescale is such that as an industrial-scale process it can be considered overall as a continuous process [a pseudo-continuous process] and thus, in this sense, the process will be subsequently described as a continuous process here.

Melt crystallisation [referred to here as a variation of Suspension crystallisation], being a well known technique for the production of high purity products, can be applied to the preparation of high purity ["Super Pure MDI" with purity>99.9% 4,4'-MDI] 4,4'-MDI as described by Koole and Goncalves ("*Continuous melt crystallisation of MDI isomers*", Netherlands Process Technology Symposium [NPS5] Theme: Engineering for Life, 25 and 26 Oct. 2005, Congress Centre NH Koningshof, Veldhoven, NL) and Zijl and Goncalves ("*Continuous melt crystallisation of MDI isomers*", Stan Ackermans Institute, University of Eindhoven, NL. 22 Nov. 2006).

However, there still remains a need for a production process operable at commercial industrial scale for the production of MDI di-isocyanate streams of defined composition which has low capital and energy costs and which can operate continuously ["pseudo-continuously"] but which is not limited to the condition that one of the MDI diisocyanate product streams has a very high [>99.9%] isomer purity.

It has now been surprisingly found that these requirements can be met by the object of the present invention which comprises a process for the simultaneous "single-step" production of two different mixtures of diisocyanate isomers of the diphenylmethane series, where the purity of both of the streams is less than 99% of any single MDI diisocyanate isomer.

The result obtained according to the present invention was particularly surprising because it had hitherto not been recognized that a process widely used specifically for the preparation of high isomer purity materials could be used in an economically beneficial and efficient way to create simultaneously two MDI isomer streams of defined composition where the purity of both of the streams is less than 99% of any single MDI diisocyanate isomer.

For the purpose of clarity it should be noted that co-production of a high or very high isomer purity stream and a lower isomer purity stream followed by the proportionate blending together of these streams or of suitable fractions of these streams to make other desirable MDI diisocyanate products or with other MDI-based products to make still further products wherever or whenever the blending is carried out can also be undertaken but such approaches are less desirable than the object of the present invention due to the requirement of extra processing steps and the associated disadvantages such as additional processing equipment and additional energy requirements.

Thus the applicants have discovered that two commercially desirable products comprising different mixtures of predominantly 4,4'-MDI and 2,4'-MDI can be produced simultaneously and continuously by economically beneficial means in a single-step melt crystallisation process whereby a mixed diisocyanate feed stream [MIx] is used to produce simultaneously two mixed diisocyanate streams [MIy and MIz] where x=80 to 92, y=97 to 99 and z=60 to 80 preferably x=82 to 88, y=97.2 to 98.5 and z=63 to 70 where x, y and z are percentages by weight of the 4,4'-MDI contained in the diisocyanate isomer mixture i.e. to produce a Pure MDI stream and a Mixed Isomer stream.

In an optional alternative embodiment, a mixed diisocyanate feed stream [MIx] is used to produce simultaneously two mixed diisocyanate streams [MIy and MIz] where x=60 to 80, y=80 to 95 and z=48 to 54 preferably x=63 to 75, y=85 to 93 and z=49 to 52 where x, y and z are percentages by weight of the 4,4'-MDI isomer contained in the diisocyanate isomer mixture. i.e. to produce two Mixed Isomers streams.

In a still further alternative embodiment, a mixed diisocyanate feed stream [MIx] is used to produce simultaneously two mixed diisocyanate streams [MIy and MIz] where x=8 to 20, y=1 to 3 and z=20 to 40 preferably x=12 to 18, y=1.5 to 2.8 and z=30 to 37 where x, y and z are percentages by weight of the 4,4'-MDI isomer contained in the diisocyanate isomer mixture.

In still further alternative embodiments, the present invention can be used in combination with other process operations for modifying MDI diisocyanate streams for example to optimise the efficiency and economy of a multi-product MDI diisocyanate and PMDI polyisocyanate manufacturing facility such as single- or multiple-column fractional distillation plant or conventional crystallisation plant such as static or dynamic crystallisers.

In still further alternative embodiments, control of the process may be achieved by on-line or off-line analysis of one or more of the product and feed streams using techniques well known to those skilled in the art such as methods based on spectroscopic techniques (UV-Vis, IR, NIR, etc.), or chromatographic techniques (gas chromatography or liquid chromatography and variations together with a range of different detection techniques etc.). Alternatively, the process may be controlled on the basis of measured temperatures, pressures, flow rates, etc. knowledge of which can be obtained by trial.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

The present invention may be understood more readily by reference to the following detailed description of preferred embodiments of the invention and the Examples included therein and to the Figures and their previous and following description.

Before the present compositions and methods are disclosed and described in detail, it is to be understood that this invention is not limited to any specific apparatus for carrying out the methods of the invention, unless so stated in the claims, as the apparatus may, of course, vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to "an impurity" includes mixtures of impurities.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

It is also to be understood that whilst the description is limited to compositions defined by their 4,4'-MDI and 2,4'-MDI contents there can, of course, in practice be small amounts of minor impurities present such as, but not limited to 2,2'-MDI, tri-isocyanate isomers, mono-isocyanates, chlorinated impurities and other halogenated impurities, methyl-group containing impurities and other impurities commonly present in process streams of these kinds.

The following description provided for clarification of the invention is given in the context of processing diisocyanate compositions where 4,4'-MDI is the major isomer present but it is to be understood that further embodiments where 2,4'-MDI is the major isomer present are also considered part of the present invention.

Figure 1:
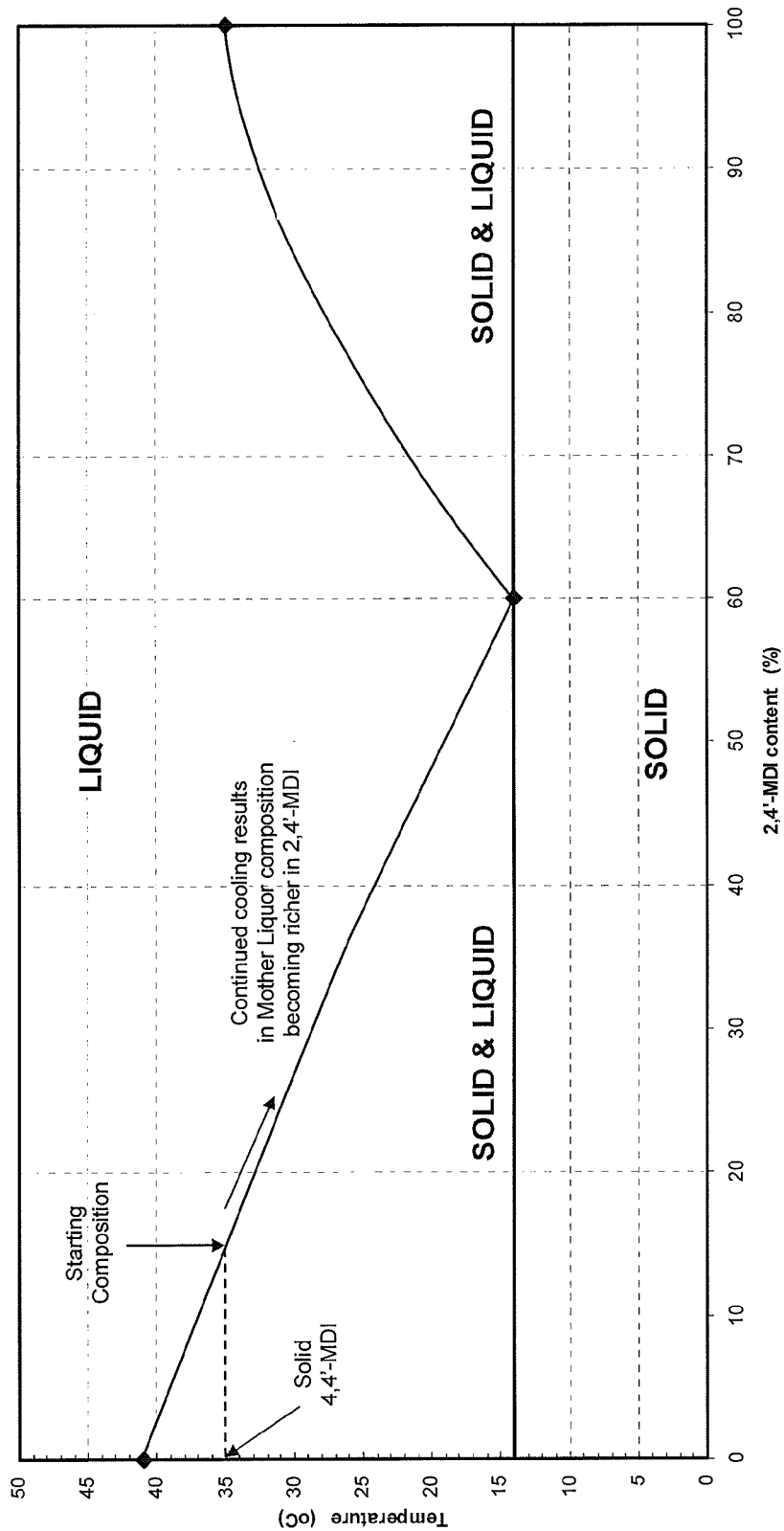
FIG. 1 is a schematic representation of the pure binary phase diagram for the 4,4'-MDI/2,4'-MDI system based on the known melting points (Ulrich, Chemistry and Technology of Isocyanates, John Wiley & Sons, New York, ISBN 0-471-96371-2) of 4,4'-MDI [41° C.], 2,4'-MDI [35° C.] and the pure binary eutectic of 40% 4,4'-MDI & 60% 2,4'-MDI [14° C.].

Fractional crystallisation processes for separating 4,4' and 2,4'-MDI isomers can generally be understood in terms of the relevant phase diagram (FIG. 1). A mixed isomer composition is cooled until solids of pure 4,4'-MDI start to form. Continued cooling results in formation of additional solid whilst the composition of the liquid phase (Mother Liquor) changes following the liquidus line of the phase diagram, becoming ever richer in the 2,4'-MDI isomer.

Note that, in practice, the presence of impurities such as 2,2'-MDI, tri-isocyanate isomers, etc. in the feed will affect the exact composition and freezing point of the last liquid to solidify. This can be determined by trial.

Figure 2:
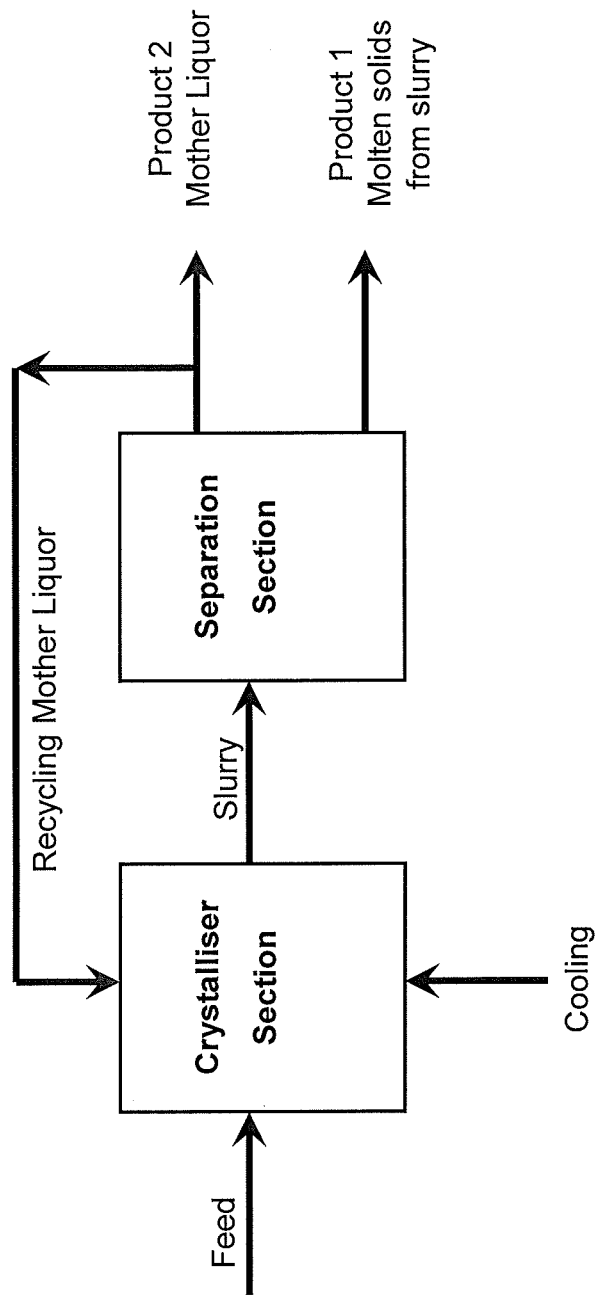
FIG. 2 is a schematic representation of a suspension crystallisation process.
Figure 3:
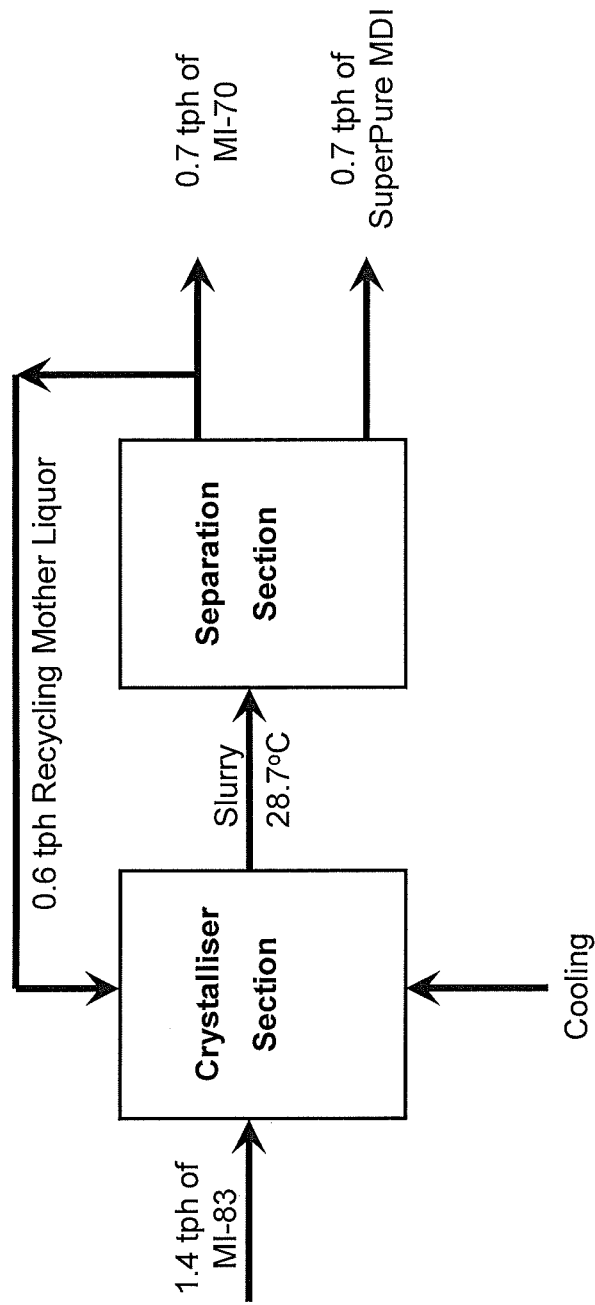
FIG. 3 is a schematic representation of the suspension crystallisation process of comparative example 1.
Figure 4:
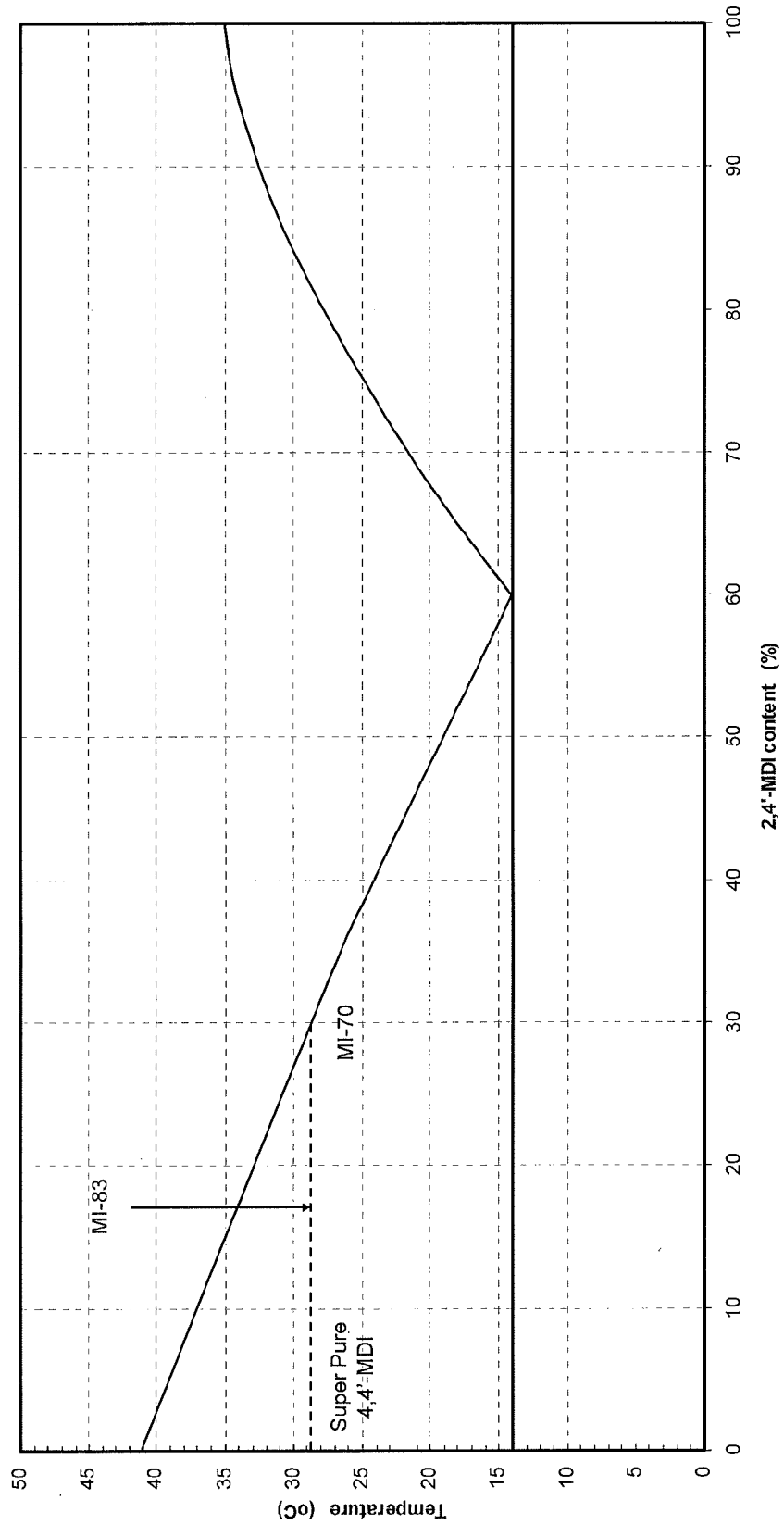
FIG. 4 is a schematic representation of the binary phase diagram for comparative example 1.
Figure 5:
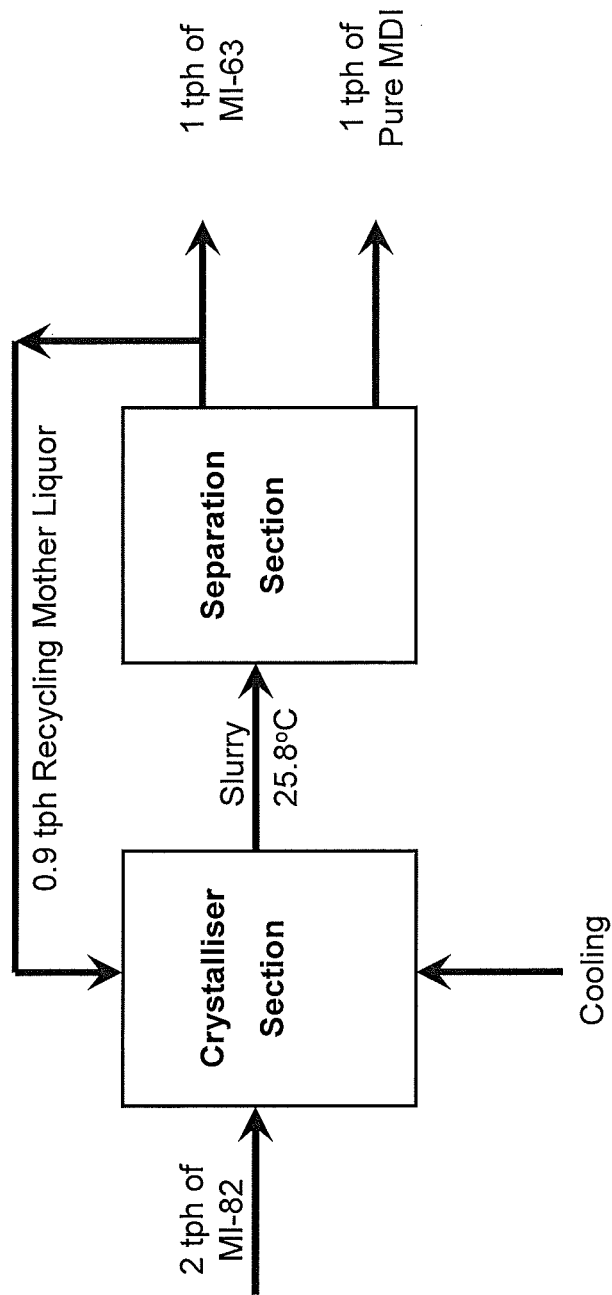
FIG. 5 is a schematic representation of the suspension crystallisation process of example 2.
Figure 6:
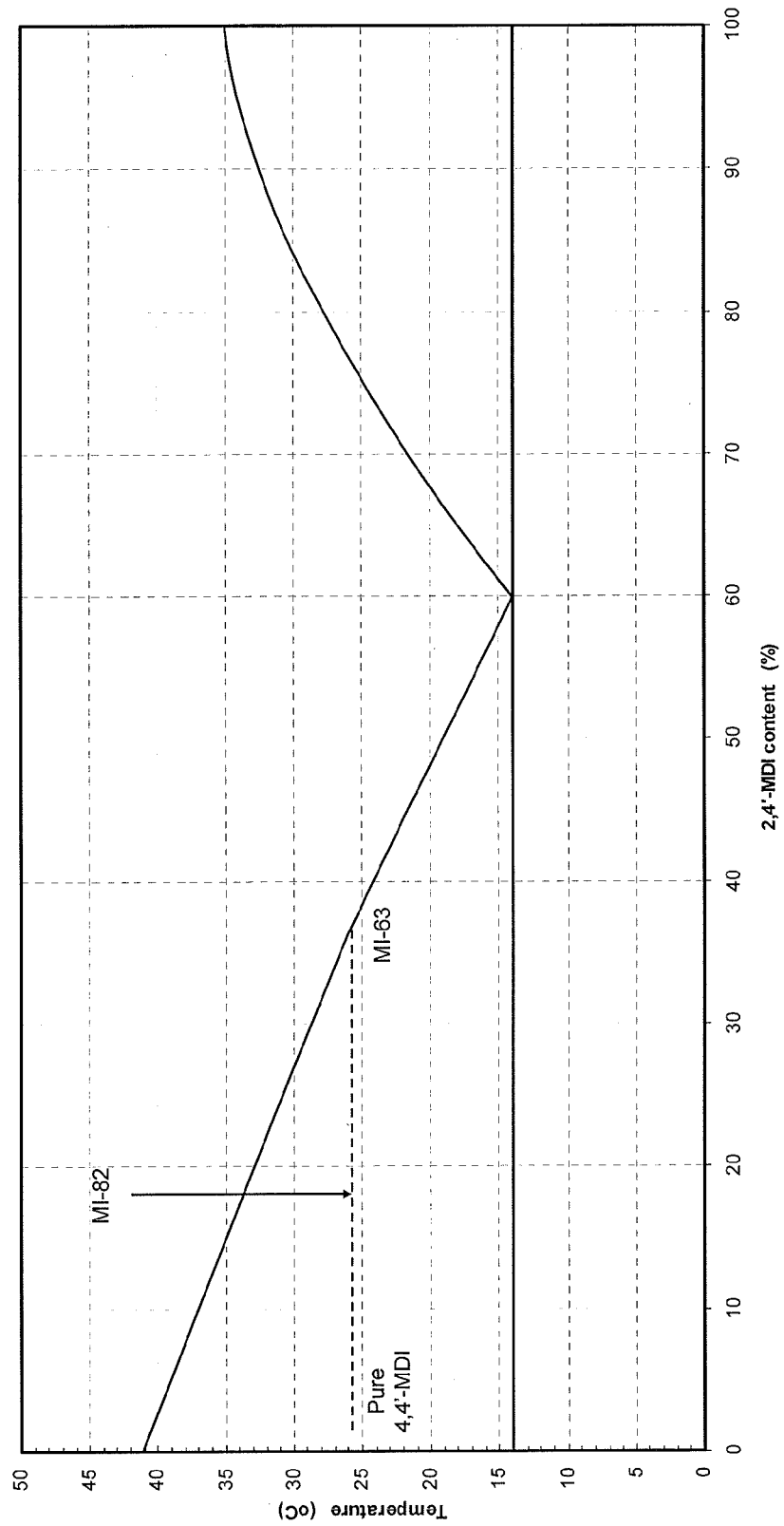
FIG. 6 is a schematic representation of the binary phase diagram for example 2.
Figure 7:
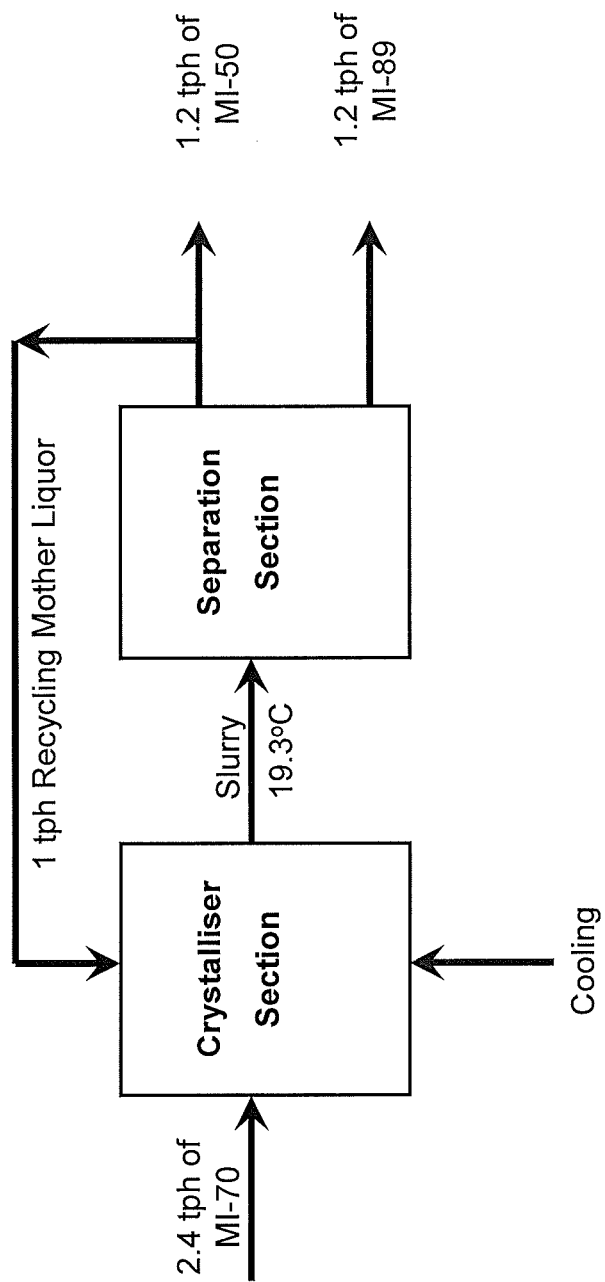
FIG. 7 is a schematic representation of the suspension crystallisation process of example 3.
Figure 8:
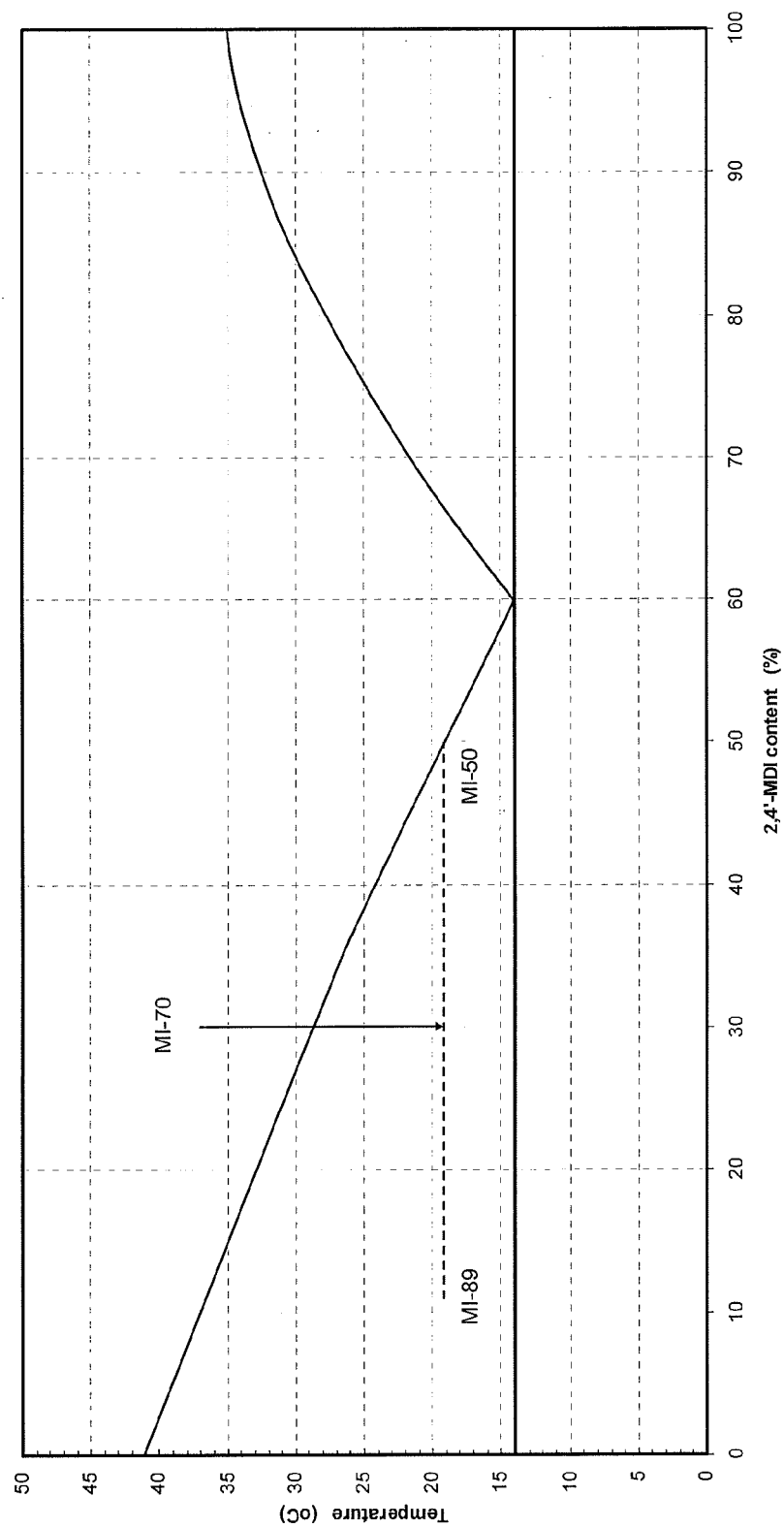
FIG. 8 is a schematic representation of the binary phase diagram for example 3.
Figure 9:
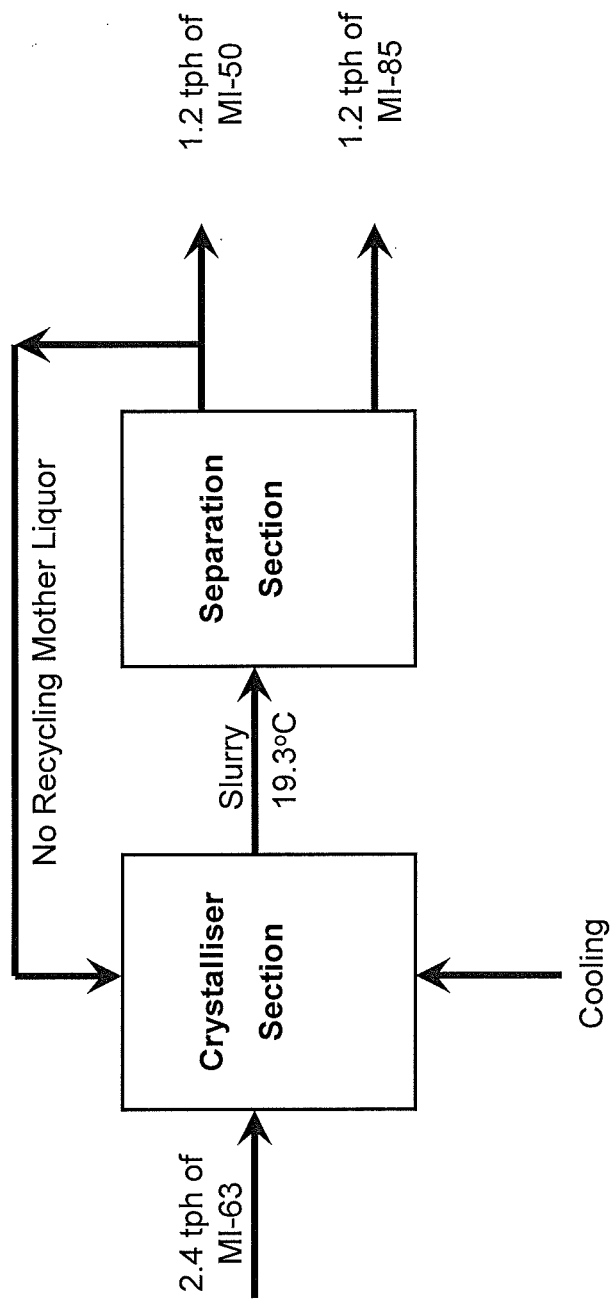
FIG. 9 is a schematic representation of the suspension crystallisation process of example 4.
Figure 10:
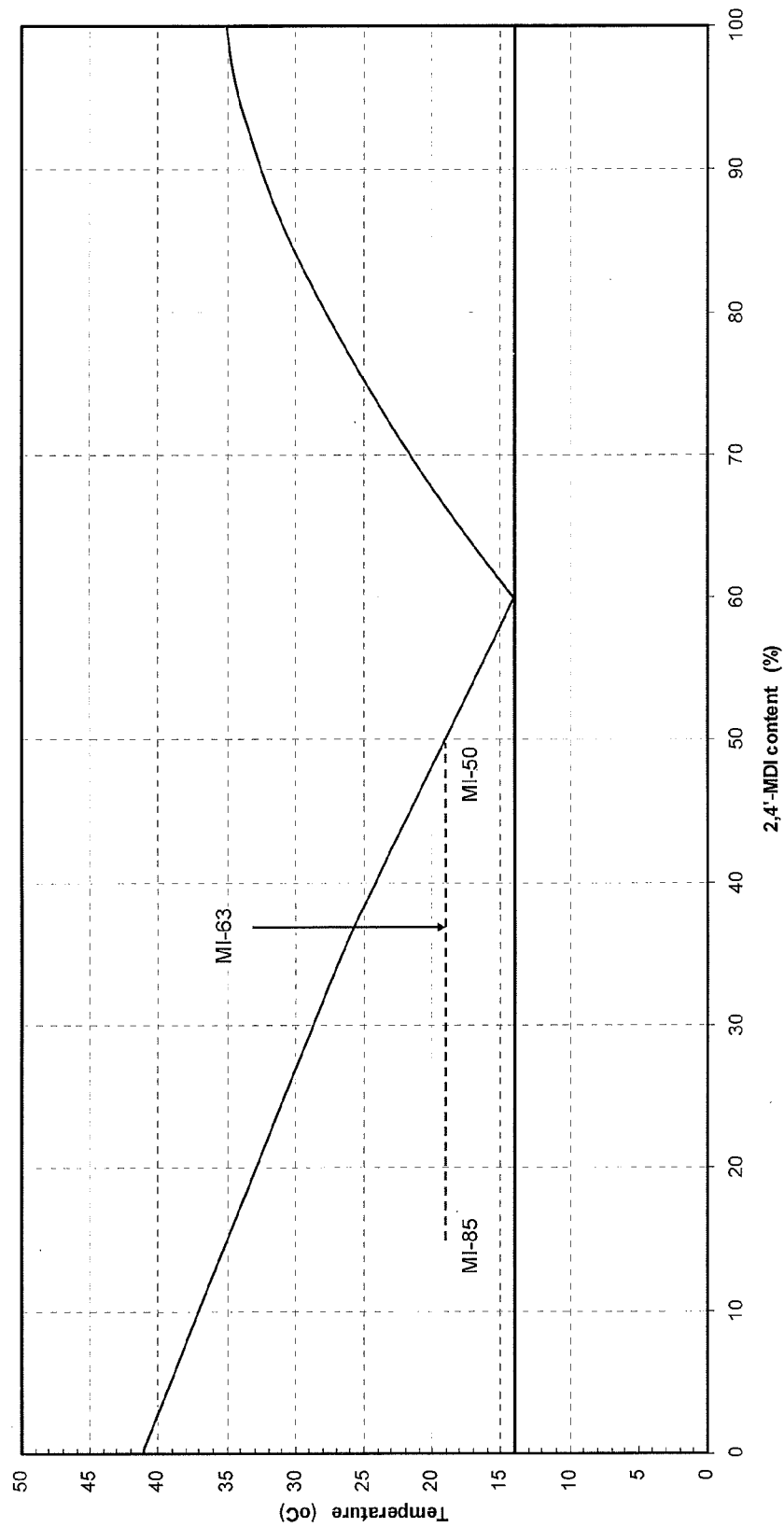
FIG. 10 is a schematic representation of the binary phase diagram for example 4.

The suspension crystallization process consists of crystallization and solid/liquid separation [wash column] sections. The crystals are formed in the crystallization section that includes a growth vessel where the crystals can grow. The crystals are separated from the liquid in the separation section, where the crystals are also melted out to form Product 1 (FIG. 2). The Mother Liquor can be split into a recycling stream and a second product stream—Product 2.

The crystallization section consists of a slurry circulation system [to circulate the slurry over the growth vessel, via the external crystallizer], a drum crystallizer [where the slurry is cooled via the cold scraped wall], a growth vessel [which provides the residence time to let the crystals grow to the required size] and an overhead feed tank [which buffers the feed and keeps the entire unit liquid full]. Alternatively, the crystallisation section could have another design for example consisting of a slurry vessel with stirrer.

The feed stream enters the crystallisation section where it is generally mixed with a Mother Liquor recycle stream. This mixture is cooled such that crystals of pure 4,4'-MDI form and grow. The temperature at this point is adjusted in order to obtain a desired slurry temperature exiting the crystallisation section. The slurry temperature is conventionally controlled by controlling the recycle flow of mother liquor to the crystaliser. However, in certain circumstances the unit may be operated without the mother liquor recycle in which case the temperature could be controlled by recirculation of some of the melted pure phase. The cooling load of the crystallizer determines the amount of crystals in the slurry. This cooling load is conventionally varied by changing the temperature of the cooling fluid. Control of the slurry temperature determines the amount of crystals formed and the composition of the liquid phase.

It is well known in suspension crystallisation processes generally that there is a limit to the maximum temperature difference [delta T] between the melting temperature of the pure phase [here 41° C. for 4,4'-MDI] and that of the slurry in order for the process to operate successfully for example to ensure formation of a stable crystal bed and well-defined wash front.

The separation section consists of a wash column system comprising a wash column and a melt loop. In practice, two such systems can be installed and operated separately such that one can be run whilst the other is not in use for example when undergoing maintenance. The two systems can also be run simultaneously for higher throughput.

The wash column is a mechanical solid-liquid separation device which is advantageous for MDI processing because the melting point of solid 4,4'-MDI is close to the temperature of slurry that is fed to it.

In steady state operating conditions the wash column contains a packed 4,4'-MDI crystal bed with above it a filter plate on a piston and below it a scraper. The voids between the upper crystals are filled with liquid with the same composition as the liquid in the crystallization section i.e. the mother liquor, which is relatively lower in 4,4'-MDI. The composition of this mother liquor is determined by the slurry temperature. The liquid in the voids between the crystals in the bottom part will be liquid that is high in 4,4'-MDI and almost pure liquid 4,4'-MDI. The place where these liquid compositions meet is called the wash front. The wash front is located somewhere within the crystal bed.

A wash column cycle, starting from this situation, can be described thus as follows:

a) Pulsation stroke: the piston moves up. Liquid is pushed out of the top compartment to the compartment below the filter plate, via piping outside the wash column.

b) Filling stroke: the piston moves even further up and creates space above the crystal bed. This space is filled with slurry from the crystallization section. The filling stroke ends when the piston reaches its top position. The liquid in the upper compartment is returned to the crystallization section or exported to a storage tank.

c) Compression stroke: The piston moves down and compresses the crystals in the slurry under the filter plate. Liquid moves from below the filter plate, through the filter plate to the upper compartment, which is increasing in volume. The compression stroke is complete when the new packed crystal bed can no longer be compressed.

d) Washing and scraping: The crystal scraper is activated after completion of the compression stroke. It scrapes crystals off the bottom of the crystal bed. These crystals are suspended in the melt with high 4,4'-MDI content that is circulating in the melt loop. Pressure is increasing in the head of the wash column, either by the melt loop pump or the piston. The pressure difference between the bottom and the top of the crystal bed makes the liquid move up through the bed. This liquid, consisting of melted almost pure 4,4'-MDI, replaces the liquid in the voids between the crystals and leaves the bottom compartment via the filter plate; the wash front is moving up. The pressures equalize and the liquid stops flowing when the wash valve opens. The wash front moves down with the crystal bed. The wash front is kept within a certain range of positions in the crystal bed by adjusting the ratio between opening and closing the product outlet valve. Washing and scraping is completed when the piston has reached its bottom position. This completes the cycle and the wash column is ready to start a new cycle.

The time required to complete a full cycle largely determines the maximum capacity of the wash column. The real capacity can be reduced by selecting a longer cycle time than the real cycle time. The wash column will then keep the piston in its bottom position, after completion of the cycle, until the selected longer cycle time has been reached, before starting a new cycle.

The melt loop consists of:

The wash column scraper: the washed crystals are scraped off the bottom and suspended in the melt loop.

The melt loop pump: this pump circulates the liquid in the melt loop and generates pressure for washing.

The melter: this heat exchanger supplies the energy to melt the crystals in the melt loop.

Thus, the overall process can be summarised as follows: Slurry is fed into the wash column, from the main circulation loop, during the filling stroke. The crystals are kept under the filter plate and the mother liquor is returned to the main circulation loop. Part of the mother liquor return is periodically sent to a storage tank to maintain a constant liquid composition and therefore a constant crystallization temperature. The crystals are scraped off the bottom of the bed in the wash column and are suspended in the melt loop. The melt of these crystals is exported to a storage tank. The overall set-up and operation of such equipment is conventionally designed to make very high purity product, in this case very high purity 4,4'-MDI [Super Pure MDI].

Surprisingly we have found that appropriate control of the slurry temperature in the crystallisation section with appropriate control of the cooling capacity of the crystalliser and with the appropriate operation of the wash column provides the solution to the problem such that the present invention provides a process for the simultaneous "single-step" production of two specific mixtures of diisocyanate isomers of the diphenylmethane series, where the purity of both of the streams is less than 99% of any single MDI isomer.

In particular we have found that by using a mixed diisocyanate feed stream [MIx] where x=80 to 92 preferably x=82 to 88 and cooling the crystallisation section whilst recycling a controlled amount of the Mother Liquor produced from the wash column such that the slurry temperature is controlled to about 25 to 27° C., we have surprisingly found that with a delta-T of about 15° C. two diisocyanate product streams [MIy and MIz] can be produced such that y=97 to 99 and z=60 to 80, preferably y=97.2 to 98.5 and z=63 to 70 where x, y and z are percentages by weight of the 4,4'-MDI isomer contained in the diisocyanate isomer mixture i.e. the composition of the melted "pure" product is less than 99.5% 4,4'-MDI. It had hitherto not been recognized that a process widely used specifically for the preparation of high isomer purity materials could be used in an economically beneficial and efficient way to create two such MDI isomer streams simultaneously.

We have also found as another embodiment that by using a mixed diisocyanate feed stream [MIx] where x=60 to 80 preferably x=63 to 75 and cooling the crystallisation section whilst recycling a controlled amount [sometimes zero] of the Mother Liquor produced from the wash column such that the slurry temperature is controlled to about 18 to 20° C., we have surprisingly found that two mixed diisocyanate product streams [MIy and MIz] can be produced such that y=80 to 95 and z=48 to 54 preferably y=85 to 93 and z=49 to 52 where x, y and z are percentages by weight of the 4,4'-MDI isomer contained in the diisocyanate isomer mixture. It had hitherto not been recognized that a process widely used specifically for the preparation of high isomer purity materials could be used in an economically beneficial and efficient way to create two MDI isomer streams simultaneously, where the composition of even the stream most enriched in one of the isomers contains at least 5% of the minor isomer.

The details of the process will now be exemplified in the following examples.

COMPARATIVE EXAMPLE 1

FIGS. 3 & 4

An MDI isomer stream containing 82.7 wt % 4,4'-MDI was fed at a rate of 1.4 ton/hr together with about 0.6 ton/hr of recycling Mother Liquor to a suspension crystallizer, comprising a drum crystallizer and a crystal growth vessel, which was controlled to a temperature of 28.7° C. creating a slurry with about 35% solids. This material was separated using one piston type wash column, into a diisocyanate isomer stream of 0.7 ton/hr with a concentration of 71.2 wt % 4,4'-MDI and a second diisocyanate isomer stream of 0.7 ton/hr containing about 99.7-99.8 wt % 4,4'-MDI [Super Pure MDI]. The delta-T was about 12° C.

EXAMPLE 2

FIGS. 5 & 6

An MDI isomer stream containing 82 wt % 4,4'-MDI was fed at a rate of 2 ton/hr together with about 0.9 ton/hr of recycling Mother Liquor to a suspension crystallizer, comprising a drum crystallizer and a crystal growth vessel, which was controlled to a temperature of 25.8° C. creating a slurry with about 35% solids. This material was separated using a set of two piston type wash columns, into a diisocyanate isomer stream of 1 ton/hr with a concentration of 63 wt % 4,4'-MDI and a second diisocyanate isomer stream of 1 ton/hr containing 98.5 wt % 4,4'-MDI [Pure MDI]. The delta-T was about 15° C.

EXAMPLE 3

FIGS. 7 & 8

An MDI isomer stream containing 70 wt % 4,4'-MDI was fed at a rate of 2.4 ton/hr together with about 1 ton/hr of recycling Mother Liquor to a suspension crystallizer, comprising a drum crystallizer and a crystal growth vessel, which was controlled to a temperature of 19.3° C. creating a slurry with about 35% solids. This material was separated using a set of two piston type wash columns, into a diisocyanate isomer stream of 1.2 ton/hr with a concentration of 50 wt % 4,4'-MDI and a second diisocyanate isomer stream of 1.2 ton/hr containing 89 wt % 4,4'-MDI.

EXAMPLE 4

FIGS. 9 & 10

An MDI isomer stream containing 62.5 wt % 4,4'-MDI was fed at a rate of 2.4 ton/hr without any recycling Mother Liquor to a suspension crystallizer comprising a drum crystallizer and a crystal growth vessel, which was controlled to a temperature of 19.3° C. creating a slurry with about 35% solids. This material was separated using a set of two piston type wash columns, into a diisocyanate isomer stream of 1.2 ton/hr with a concentration of 50 wt % 4,4'-MDI and a second diisocyanate isomer stream of 1.2 ton/hr containing 85 wt % 4,4'-MDI.

Figure 11:
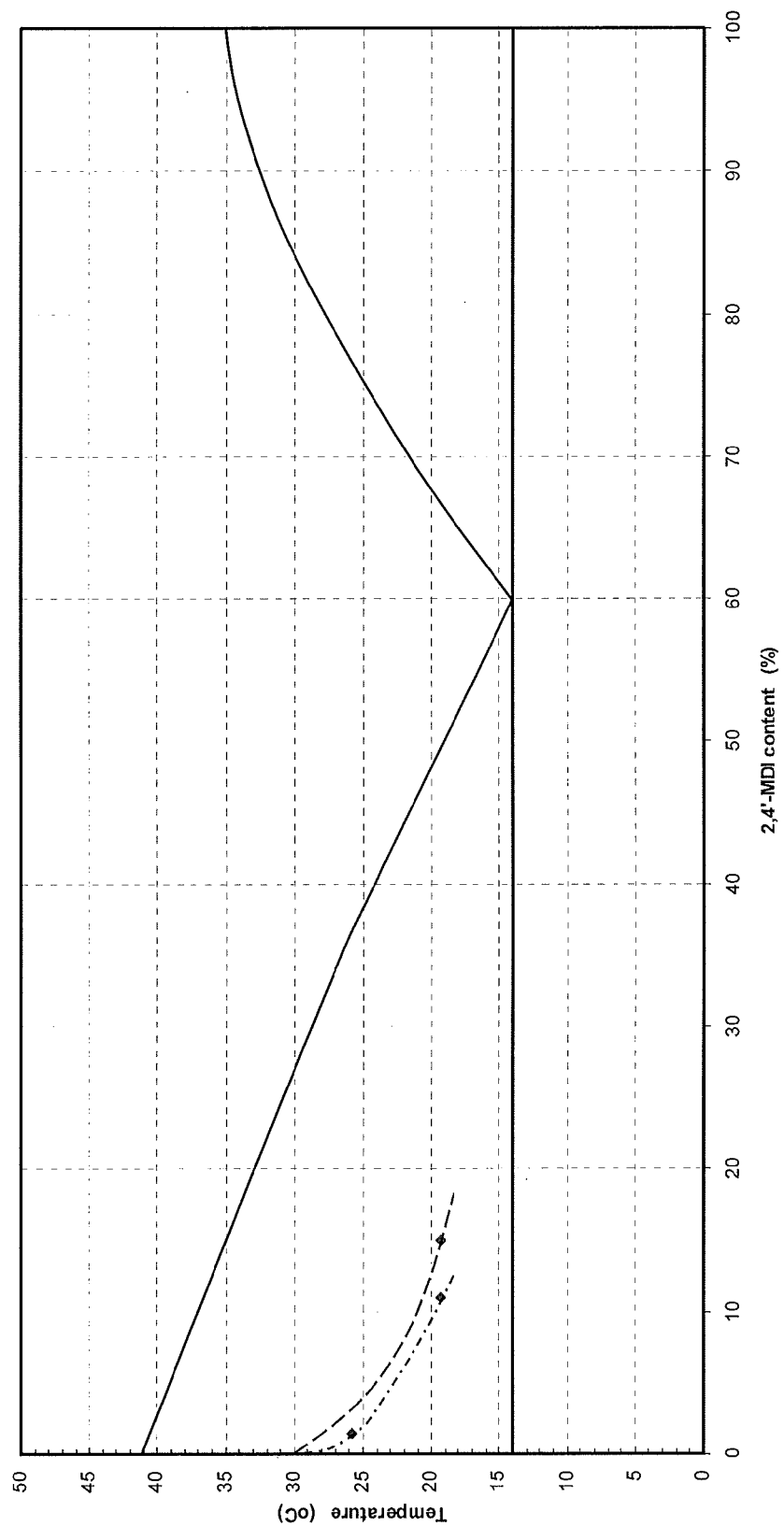
FIG. 11 is a schematic representation of the pure binary phase diagram for the 4,4'-MDI/2,4'-MDI system illustrating one or more "working lines".

It is apparent that these results exemplifying the invention illustrate the existence of one or more "working lines" on the phase diagram [FIG. 11] possibly reflecting the effect of operating conditions on the formation, growth and separation characteristics of the 4,4'-MDI crystals. The existence and use of these "working lines" are also a feature of the present invention. No meaning other than "working line" such as solidus, "pseudo-solidus", "solid-state solution" or other is intended or implied by the addition of these lines to the phase diagram.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

The invention claimed is:

1. A process for the simultaneous and continuous production of a first isomer mixture and a second isomer mixture wherein each of the mixtures comprises predominantly of 4,4'-diphenylmethane diisocyanate and 2,4'-diphenylmethane diisocyanate comprising the step of separating a mixed diphenylmethane diisocyanate isomer feed stream [MIx] by a single-step suspension melt crystallisation process into two mixed isomer diphenylmethane diisocyanate streams [MIy and MIz] thereby forming a slurry in a crystallisation section, wherein the melt crystallisation process comprises a crystallization step wherein crystals [MIy] are formed in a mother liquid [MIz], wherein the slurry exits the crystallisation section and the mother liquid is subjected to a subsequent separation step whereby one or more crystals are melted out of the mother liquid to form the first isomer mixture and the remaining mother liquid is split into the second isomer mixture and a recycling stream, wherein the recycling stream is fed back into the crystallisation section, wherein x is 80 to 92, y is 97 to 99 and z is 60 to 80 where x, y and z are percentages by weight of the 4,4'-diphenylmethane diisocyanate isomer contained in the diphenylmethane diisocyanate isomer mixture; and wherein the temperature of the slurry exiting the crystallisation section is controlled to about 25° C. to 27° C.

2. The process according to claim 1 wherein x is 82 to 88, y is 97.2 to 98.5 and z is 63 to 70.

3. A process for the simultaneous and continuous production of a first isomer mixture and a second isomer mixture wherein each of the mixtures comprises predominantly of 4,4'-diphenylmethane diisocyanate and 2,4'-diphenylmethane diisocyanate comprising the step of separating a mixed diphenylmthane diisocyanate isomer feed stream [MIx] by a single-step suspension melt crystallisation process into two mixed isomer diphenylmethane diisocyanate streams [MIy and MIz] thereby forming a slurry in a crystallization section, wherein the melt crystallisation process comprises a crystallisation step wherein crystals [MIy] are formed in a mother liquid [MIz], wherein the slurry exits the crystallisation section and the mother liquid is subjected to a subsequent separation step whereby one or more crystals are melted out of the mother liquid to form the first isomer mixture and the remaining mother liquid is split into the second isomer mixture and a recycling stream, wherein the recycling stream is fed back into the crystallisation section, wherein x is x is 60 to 80, y is 80 to 95 and z is 48 to 54 where x, y and z are percentages by weight of the 4,4'-diphenylmethane diisocyanate isomer contained in the diphenylmethane diisocyanate isomer mixture; and wherein the temperature of the slurry exiting the crystallisation section is controlled to about 18° C. to 20° C.

4. The process according to claim 3 wherein x is 63 to 75, y is 85 to 93 and z is 49 to 52.

5. A process for the simultaneous and continuous production of a first isomer mixture and a second isomer mixture wherein each of the mixtures comprises predominantly of 4,4'-diphenylmethane diisocyanate and 2,4'-diphenylmethane diisocyanate comprising the step of separating a mixed diphenylmethane diisocyanate isomer feed stream [Mix] by a single-step suspension melt crystallisation process into two mixed isomer diphenylmethane diisocyanate streams [MIy and MIz] thereby forming a slurry in a crystallisation section, wherein the melt crystallisation process comprises a crystallisation step wherein crystals [MIy] are formed in a mother liquid [MIz], wherein the slurry exits the crystallisation section and the mother liquid is subjected to a subsequent separation step whereby one or more crystals are melted out of the mother liquid to form the first isomer mixture and the remaining mother liquid is split into the second isomer mixture and a recycling stream, wherein the recycling stream is fed back into the crystallisation section, wherein x is 8 to 20, y is 1 to 3 and z is 20 to 40 where x, y and z are percentages by weight of the 4,4'-diphenylmethane diisocyanate isomer contained in the diphenylmethane diisocyanate isomer mixture.

6. Process according to claim 5 wherein x is 12 to 18, y is 1.5 to 2.8 and z is 30 to 37.

* * * * *